United States Patent
Kaasinen et al.

(10) Patent No.: US 10,595,778 B2
(45) Date of Patent: Mar. 24, 2020

(54) WEARABLE GARMENT AS WELL AS A SYSTEM AND METHOD FOR DETERMINING THE SUPPORT PROVIDED BY A WEARABLE GARMENT

(71) Applicant: Suunto Oy, Vantaa (FI)

(72) Inventors: Jussi Kaasinen, Vantaa (FI); Erik Lindman, Vantaa (FI); Mikko Martikka, Vantaa (FI)

(73) Assignee: Suunto Oy, Vantaa (FI)

( * ) Notice: Subject to any disclaimer, the term of this patent is extended or adjusted under 35 U.S.C. 154(b) by 181 days.

(21) Appl. No.: 15/857,680

(22) Filed: Dec. 29, 2017

(65) Prior Publication Data

US 2018/0184975 A1 Jul. 5, 2018

(30) Foreign Application Priority Data

Dec. 30, 2016 (FI) .................................. 20166048
Dec. 30, 2016 (GB) ................................. 1622418.0

(51) Int. Cl.
| | |
|---|---|
| *A61B 5/00* | (2006.01) |
| *A61B 5/024* | (2006.01) |
| *A61B 5/11* | (2006.01) |
| *A61B 5/0255* | (2006.01) |
| *A41C 3/00* | (2006.01) |

(52) U.S. Cl.
CPC .......... *A61B 5/6804* (2013.01); *A61B 5/0002* (2013.01); *A61B 5/0255* (2013.01); *A61B 5/02438* (2013.01); *A61B 5/11* (2013.01); *A41C 3/0057* (2013.01); *A61B 2562/0219* (2013.01)

(58) Field of Classification Search
CPC ....... A61B 5/6804; A61B 5/0002; A61B 5/11; A61B 5/0255; A61B 5/02438; A61B 2562/0219; A41C 3/0057
See application file for complete search history.

(56) References Cited

U.S. PATENT DOCUMENTS

| | | | |
|---|---|---|---|
| 6,198,204 B1 * | 3/2001 | Pottenger ............. | A41C 3/0057 310/326 |
| 2008/0133171 A1 | 6/2008 | Feichtinger et al. | |
| 2009/0287191 A1 * | 11/2009 | Ferren .................. | A61B 5/0031 604/891.1 |

(Continued)

FOREIGN PATENT DOCUMENTS

| | | |
|---|---|---|
| CN | 103445787 A | 12/2013 |
| FI | 20136346 A | 7/2015 |
| WO | WO2011056765 A1 | 5/2011 |

OTHER PUBLICATIONS

Cionca et al: TDMA Protocol Requirements for Wireless Sensor Networks. The Second International Conference on Sensor Technologies and Applications, Aug. 2008, pp. 30-35.

(Continued)

*Primary Examiner* — Catherine M Voorhees
(74) *Attorney, Agent, or Firm* — Laine IP Oy (57) ABSTRACT

A solution is offered to providing wearable garment, which provides a continued support for the wearer. A novel system is proposed including a wearable garment and a sensor module attached to the wearable garment. The sensor module has an oscillation sensing element, which measures oscillations experienced by the wearable garment, and an interface provided to the oscillation sensing element for outputting measurement data to a processor.

29 Claims, 5 Drawing Sheets

(56) References Cited

U.S. PATENT DOCUMENTS

| | | | |
|---|---|---|---|
| 2013/0060349 A1 | 3/2013 | Thorsteinsson et al. | |
| 2013/0085538 A1 | 4/2013 | Volpe et al. | |
| 2013/0217979 A1 | 8/2013 | Blackadar et al. | |
| 2014/0287652 A1* | 9/2014 | Deguchi | A41C 3/0021 |
| | | | 450/86 |
| 2014/0318699 A1* | 10/2014 | Longinotti-Buitoni | |
| | | | A61B 5/0002 |
| | | | 156/247 |
| 2015/0226574 A1 | 8/2015 | Takakura et al. | |
| 2015/0342266 A1 | 12/2015 | Cooper et al. | |
| 2015/0366504 A1 | 12/2015 | Connor | |
| 2016/0220808 A1 | 8/2016 | Hyde et al. | |
| 2016/0249698 A1* | 9/2016 | Berzowska | A41D 13/0015 |
| | | | 2/69 |
| 2017/0202271 A1* | 7/2017 | Stasey | A41C 3/0057 |

OTHER PUBLICATIONS

University of Portsmouth: Bouncing breasts spark new bra challenge. Sciencedaily, Sep. 23, 2007, <www.sciencedaily.com/releases/2007/09/070915124901.htm>.

Campbell et al: Can fabric sensors monitor breast motion? Journal of Biomechanics, 2007, vol. 40, No. 13, pp. 3056-3059.

\* cited by examiner

WEARABLE GARMENT AS WELL AS A SYSTEM AND METHOD FOR DETERMINING THE SUPPORT PROVIDED BY A WEARABLE GARMENT

FIELD

The present disclosure relates to wearable garments, such as sports bras. In particular, the present disclosure relates to determining the sufficiency of support provided by a wearable garment.

BACKGROUND

Wearable garments intended for active use are typically designed to make the wearer as comfortable as possible during a particular activity. Examples include sports bras, which are made from a breathable and supple fabric, which is pleasant to wear. The fabric is also cut and possibly reinforced to provide ample support for the wearer's breast during physical exercise. The support provided by the garment is important for minimizing the fatiguing effect of reciprocal movement on the body. Accordingly, garments have been optimized for providing the best possible support possible. U.S. Pat. No. 6,198,204 B1, for example, discloses a sports bra with an integrated piezoelectric transducer, which senses movements of the breast and stiffens the piezoelectric transducer so as to provide more support for the breast in the event that the detected movement exceeds a predetermined limit.

The performance of conventional wearable garments, particularly sports bras, is primarily based on the aforementioned fit and elastic properties of the product. Taking a sports bra as an example it is not uncommon that the fit changes during the lifetime of the product due to change in breast size or shape as a result of pregnancy, for example, or the elastic material loses some of its elastic properties due to fatigue, creeping or both. It is therefore desirable to provide a wearable garment, which provides continued support for the wearer regardless of the prevailing circumstances.

SUMMARY

The present solution offers a solution to providing wearable garment, which provides continued support for the wearer. A novel system is proposed including a wearable garment, a sensor module attached to the wearable garment, a memory for logging the measurement data and a processor for processing the logged measurement data received via an interface on the sensor module. The sensor module has an oscillation sensing element, which measures oscillations experienced by the wearable garment, and an interface provided to the oscillation sensing element for outputting measurement data to a processor.

On the other hand a novel method is proposed for computing the sufficiency of support provided by a wearable garment, which includes a sensor module measuring oscillations experienced by the wearable garment over a first time frame. An output is formed of the measurement data for a processor and the measurement data is processed with the processor into an index value representative of the support provided by the wearable garment.

According to a further aspect, a non-transitory computer readable medium is proposed having stored thereon a set of computer readable instructions that, when executed by at least one processor, cause an apparatus to at least receive oscillation measurement data, and to process the measurement data with the processor into an index value representative of the support provided by a wearable garment.

The invention is defined by the features of the independent claims. Some specific embodiments are defined in the dependent claims.

BRIEF DESCRIPTION OF THE DRAWINGS

In the following certain embodiments are described in greater detail with reference with the accompanying drawings, in which.

DETAILED DESCRIPTION OF EXEMPLARY EMBODIMENTS

Figure 1:
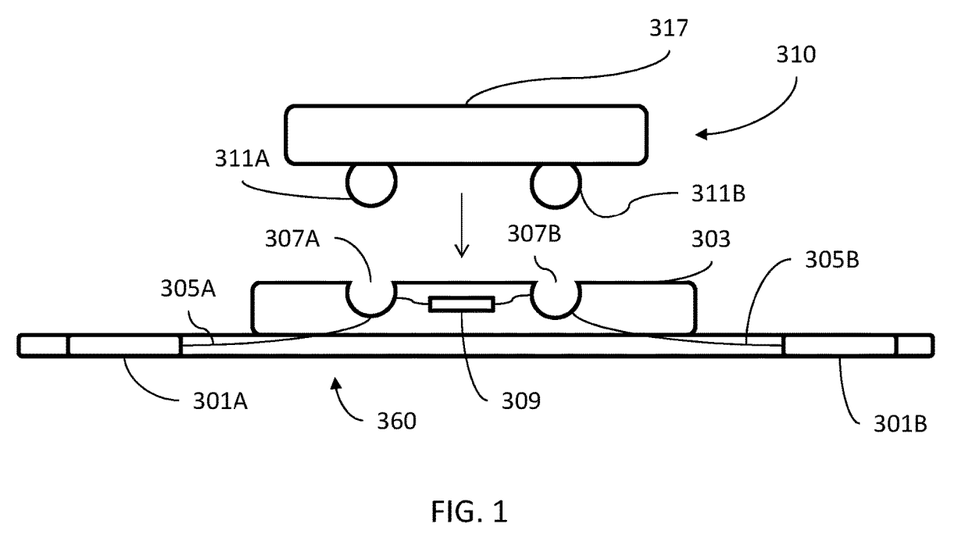
FIG. 1 illustrates a schematic diagram of a wearable garment in accordance with at least some embodiments of the present invention.

According to the illustrated embodiment, a system is proposed featuring a wearable garment with a built-in or detachable and particularly interchangeable sensor module, which may be used in connection with several such wearable garments. Exemplary wearable garments benefitting from the novel arrangement for monitoring the sufficiency of support include brassieres, sport bras, compression clothing, e.g. compression socks, gaiters, leggings, etc. The interchangeability yields the benefit of being able to track the sufficiency of support of several garments of different appearance, age, purpose, etc. Accordingly, a system for determining the support provided by a wearable garment is proposed. FIG. 1 illustrates two key components of such a system, namely the sensor module 310 and wearable garment 360 in more detail. The sensor module 310 comprises a housing 317 and two electric contact terminals 311A, 311B on the outer surface of the housing. In this example, the contact terminals 311A, 311B are in the form of bumps or buttons capable of being snapped into suitable recess counterparts 307A, 307B of a mounting zone 303 of a wearable garment 360 to provide both attachment and electric connection. There may also be provided separate or additional means to take care of these functions.

Alternatively, the sensor module 310 could be built-in to the wearable garment. For example, the sensor module could be sewn in between two plies of fabric of a sports bra, piece of compression clothing, etc. Any feature herein described is applicable to an integrated sensor module. Similarly, the wearable garment may comprise integrated heart rate sensors or attachable heart rate sensors. Also, any combination of an integrated or attachable heart rate sensors and an integrated or attachable sensor module is foreseen. However, for the purpose of illustrating certain embodiments, a detachable sensor module is depicted.

Figure 2:
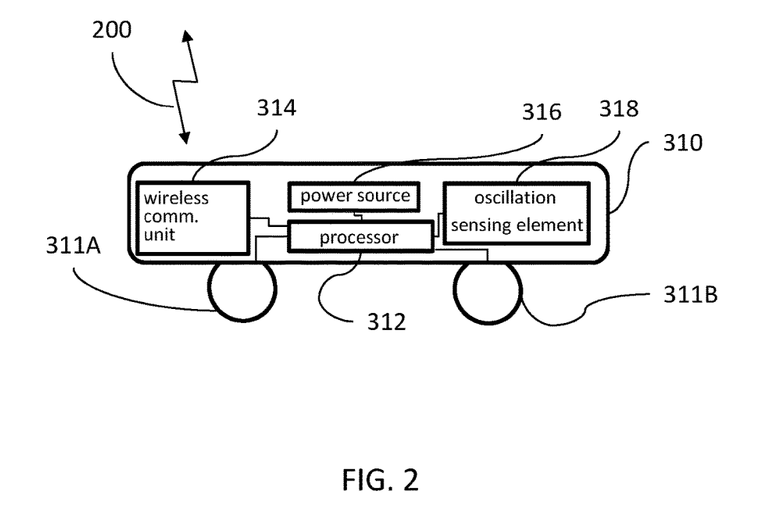
FIG. 2 illustrates schematic diagram of the sensor module of FIG. 1.

In the mounting zone 303, there may provided an identification module 309 electrically connected to the counterparts 307A, 307B. Thus, when the sensor module 310 is connected to the mounting zone 303, it is able to access the identification module 309 and read the identifier stored therein. Alternatively, the communication interface between the identification module and the sensor module may be wireless. Whether wired as shown in FIGS. 1 and 2 or wireless, the communication interface between the identification module 309 and the sensor module 310 is configured to communicate the identification data between the modules 309, 310. Accordingly, the sensor module 310 is configured to read the identification data from the identification module 309 via the communication interface. In this example, the counterparts 307A, 307B are additionally connected to EMG, ECG or heart rate sensor pads 301A, 301B using suitable wirings 305A, 305B in the wearable garment 360 to provide a biosignal, such as an ECG or an EMG signal, to the module 310. The identification module 309 may comprise a memory circuit and a suitable interface circuit. A memory read command can be sent from the sensor module to the interface circuit to read the identifier. The module may distinguish between identifier data and sensor input data by frequency characteristics of the signals.

As an alternative to the illustrated wired identification module reading, the reading may take place wirelessly. For example, there may be a radio-frequency identification (RFID) tag, such as a near-field communication (NFC) tag embedded in the mounting zone and the module contains a corresponding RFID/NFC reader unit for reading the identifier. In this case, the contact terminals of the module serve for sensor signal reading only.

If the wearable garment contains a local processor for processing sensor and/or actuator data, the identification module can be integral with that processor or memory used by the processor.

FIG. 2 shows in more detail the main internal components of a sensor module 310 according to one embodiment. The sensor module 310 comprises a processor 312 which controls and processes the input and output of the module via a wireless communication unit 314 (to and from a monitoring unit) and the contact terminals 311A, 311B (towards an identifier and sensor in a wearable garment). There may provided a separate input and/or output unit (not shown) between the processor 312 and the contact terminals 311A, 311B, the input and/or output unit comprising the necessary circuits for amplification of the input signals, if needed.

The processor 312 typically comprises a microcontroller operated by firmware, and an amount of memory. One example of a suitable microcontroller is a Nordic Semiconductor nRF52832 comprising 32 bit ARM® Cortex®-M4 with 64 kB on-chip RAM and 512 kB on-chip FLASH, an external memory and a 128 kB EEPROM (Atmel AT24CM01) link. There may also be a separate memory circuit (not shown) for storage of larger amounts of data. Tasks of the processor 312 include performing internal data processing actions of the sensor module 310 and controlling communication to/from the monitoring unit and the wearable garment the module is attached to. Also, the processor may execute the processing instructions selected on the basis of the ID read from the wearable garment 360.

The wireless communication unit 314 comprises an antenna and necessary electronics for amplification of the received and transmitted signals and for coupling with the processor 312. The communication unit 314 can utilize any desired wireless communication protocol. The protocol is preferably a time slot-based protocol. Examples of suitable protocols include like Bluetooth LE and ANT+, using direct-sequence spread spectrum (DSSS) modulation techniques and an adaptive isochronous network configuration, respectively. A thorough description of the necessary hardware for various implementations is available e.g. from the Texas Instrument®'s handbook "Wireless Connectivity" which includes IC circuits and related hardware configurations for protocols working in sub-1- and 2.4-GHz frequency bands, such as ANT™, Bluetooth®, Bluetooth low energy, RFID/NFC, PurePath™ Wireless audio, ZigBee®, IEEE 802.15.4, ZigBee RF4CE, 6LoWPAN, Wi-Fi®, GPS.

For example, in the case of Bluetooth LE, an Attribute Profile (ATT) wire application protocol is used. An attribute is composed of three elements: a 16-bit handle; an UUID which defines the attribute type; a value of a certain length. A handle is a number that uniquely identifies an attribute and is expected to be stable for each device. A UUID (universally unique identifier) is an identifier standard used in software construction to enable distributed systems to uniquely identify information without significant central coordination. The value is an array of bytes of any size. The meaning of the value depends on the UUID. Also TDMA-based protocols may be used, as discussed in "TDMA Protocol Requirements for Wireless Sensor Networks", Sensor Technologies and Applications, SENSORCOMM '08. Second International Conference on. 25-31 Aug. 2008, Pages 30-35, ISBN: 978-0-7695-3330-8.

Figure 3:
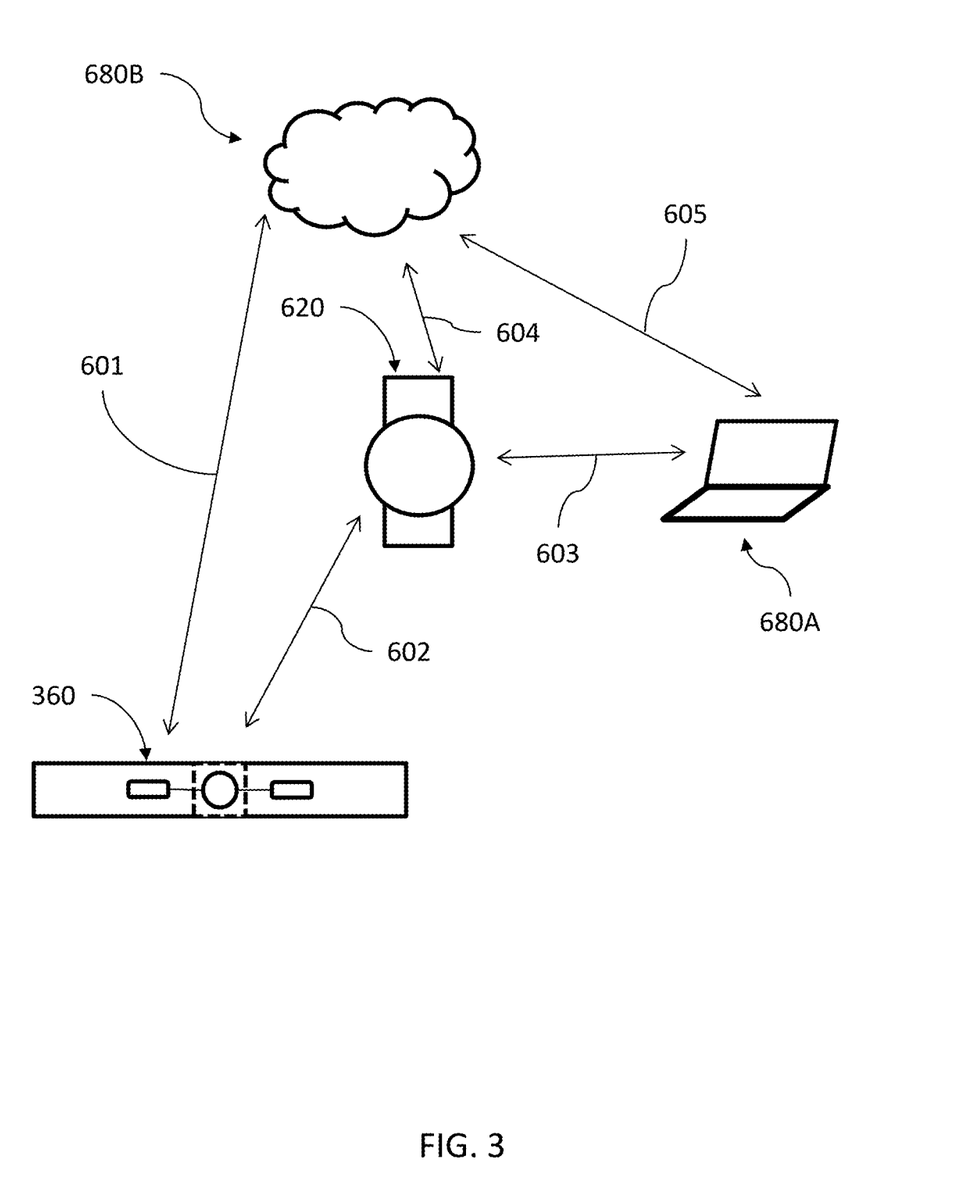
FIG. 3 illustrates a schematic diagram of the wearable garment of FIG. 1 in communication with external devices.

Accordingly, the wireless communication unit 314 may transmit and receive data to and from an external source, such as a server or a terminal device or both either directly or indirectly. For example, the sensor module 310 may communicate with a server via a wireless link 200 wither directly or through a terminal device, such as a smart phone, tablet, smart watch, etc. FIG. 3 shows an exemplary illustration of one foreseeable network. The wearable garment 360 may communicate with a cloud or server 680B directly via a wireless link 601 provided by the wireless communication unit 314. Alternatively, the traffic may be routed through a terminal device 620, such as a smart watch or smart phone or similar via a wireless link 602 between the wearable garment 360 and the terminal device 620 and wireless link 604 between the terminal device 620 and the cloud or server 680B. Particularly, data may be delivered from the sensor module 310 first to a terminal device 620, such as a smart watch, and then directly or via a second terminal device (not shown), such as a mobile phone, to a web server 680B. In such an embodiment, the first terminal device need not be equipped with a mobile data connection to a web server. Instead, the first terminal device may perform only light processing to the measurement data, whereas the majority of the data processing and traffic to and from a web server may be carried out in a second terminal device better equipped for the task. Also, the further processing steps and/or transmission of data may be performed at a later stage in respect to the measuring step. Furthermore, the traffic may be routed through another computing device 680A, such as a personal computer or another server via a wireless link 603 between the terminal device 620 and the computing device 680A and wireless link 605 between the computing device 680A and the cloud or server 680B. Other networks are foreseeable including replacing one or several links with wired connections.

By virtue of the wireless communication unit 314 the program controlling the sensor module 310 may be stored on a built-in memory or an external memory on an external device, such as a terminal device, e.g. a smart phone etc., or a server or cloud or similar.

The sensor module 310 is powered by a power source 316, most typically a battery. There are also means (not show) for charging or allowing for changing the battery. The sensor module 310 also includes an oscillation sensing element 318, such as an accelerometer, connected to the processor 312. According to one embodiment, the oscillation sensing element 318 comprises an accelerometer, particularly a multi-axis accelerometer, such as a nine-axis accelerometer, a piezoelectric element configured to deform in response to the deformation of the fabric of the wearable garment during oscillations, a gyroscope, or any combination of the afore-mentioned. The oscillation sensing element 318 is configured to sense the oscillations experienced by the wearable garment 360 and to output the measurement data for the processor 312 for processing or for transmission to an outside processor for processing. The processing may therefore take place in the sensor module 310 or an external device, such as a server, smart phone, tablet, smart watch, etc., via the wireless link 200. Accordingly the interface between the oscillation sensing element 318 and the processor may be seen as the wired connection between the oscillation sensing element 318 and the processor 312 shown in FIG. 2 or as the chain of said wired connection and the wireless link 200.

One example of a sensor module 310 suitable for use in the proposed application is a Movesense sensor or a Suunto Smart Sensor 1.1. The sensor module 310 preferably includes a nine-axis motion sensor, in-built memory for logging data and a wireless communication unit, particularly a Bluetooth interface and even wireless update capability.

The sensor module 310 is configured to aid a calculatory process of determining the sufficiency of support provided by the wearable garment 360. The process is particularly useful in monitoring the performance of the wearable garment 360 in respect to aging of the product, changes in the anatomy of the user, in fitting the product, or in any combination the afore-mentioned situations. The process may therefore be continuous over the lifetime of the product or an isolated event in fitting the product.

The method of computing the sufficiency of support provided by the wearable garment 360 basically includes three main phases; firstly measuring 402 oscillations with the sensor module 310, secondly forming an output of the measurement data for a processor, and thirdly processing the measurement data with the processor into an index value representative of the support provided by the wearable garment 360. On a general level it may be noted that processing phase may be performed locally in the sensor module 310, particularly by the processor 312 of the sensor module 310, or externally in a terminal device 620, such as a smart phone, smart watch, etc., or in a server, cloud 680B, computed 680A or similar network resource. For facilitating external processing it is preferable that the sensor module 310 comprises a sufficient amount of memory for compiling measurement data and an efficient communication interface, such as any of the afore-mentioned options for a wireless communication unit 314 for transmitting the measurement data for external processing. In the following example, the processing is described to take place in a smart terminal device 620.

Figure 4:
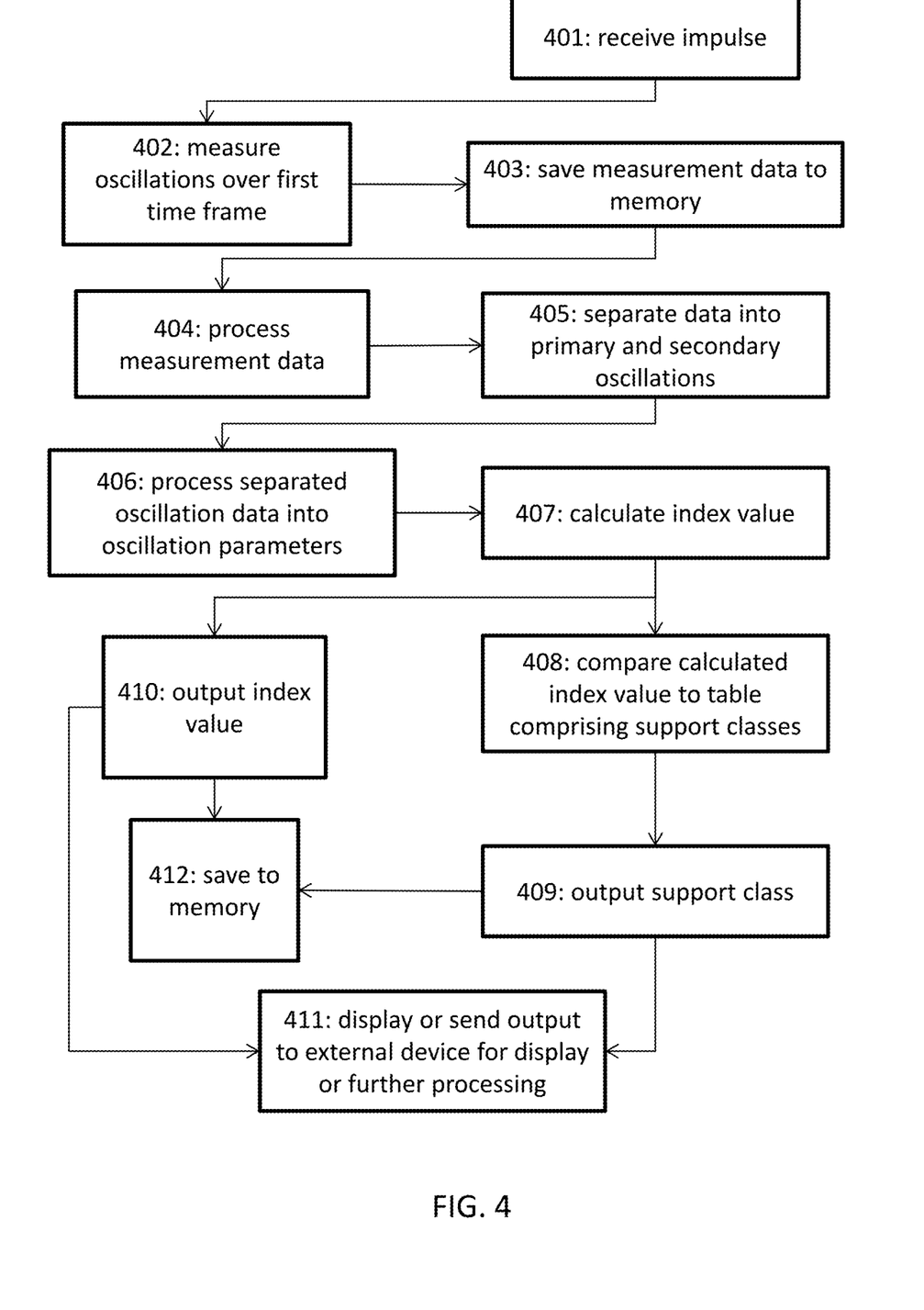
FIG. 4 is a flow graph showing method steps according to one embodiment.

Reference is first made to FIG. 4, which shows an exemplary illustration of a method according to one embodiment of the method. The process begins with an impulse 401 received by the processor 312 of the sensor module 310 to begin measuring oscillations. The impulse may be, for example, an input from a simple I/O interface (not shown) on the sensor module 310, such as a button, a command from the terminal device 620 via the wireless communication unit 314, detection of a shock, i.e. acceleration, exceeding a limit set for beginning the process or other input. The oscillation sensing element 318 measures 402 oscillation data over a first time frame. The measurement data may be transmitted out of the sensor module 310 to be stored and processed externally, the data may be buffered into the memory of the sensor module 310 and sent out in batches or all at once, or the buffered data may be pre-processed in the sensor module 310 or processed completely be the sensor module 310. In a particular embodiment, the oscillation data measured over the first time frame is saved 403 into the local memory in the sensor module 310 and sent for external processing.

Next the data is processed 404 for example externally in a terminal device or locally in the sensor module 310. The measurement data is preferably pre-processed by filtering out unnecessary data sections, such as static in the oscillation measurement data or low or high frequency bands. The oscillation data is then separated 405 into primary and secondary oscillations. The oscillation data is processed into oscillation parameters, such as frequency, amplitude and/or phase prior to separation into primary and secondary oscillations or afterwards 406, as depicted in FIG. 4.

The oscillations are recorded with the oscillation sensing element 318, which may take the form of an accelerometer. The oscillation data is recorded in a time frame showing the amplitude and frequency of the oscillation. From this data it may be computed that there may exist prominent amplitudes occurring at a given point in time. These prominent amplitudes are the result of the user moving during exercise. The oscillation occurring at a higher amplitude range is derived as the primary oscillation, i.e. the zero phase oscillation acting as stimulus or excitation for the secondary oscillation. Prominent amplitudes occurring at multiple frequencies in respect to the primary oscillations are derived as the secondary oscillations. The secondary oscillations detected by the sensor module 310 are the result of tissue of the user oscillating at a smaller amplitude range due to inertia. The inertia of the tissue may also cause the tissue to oscillate later than what the primary oscillation would indicate. Accordingly, there may be a phase shift between the primary and secondary oscillation.

According to one embodiment, the primary and secondary oscillation data may originate from different sensors. It may be, for example, that the primary oscillation data is recorded by a sensor attached to one wearable garment, such as a running shoe, or to a terminal device, such as smart watch, which is attached to the user such that there is no or minimal respective movement between the user and garment or terminal device. The secondary oscillation data may originate from a second wearable garment, such as a sports bra, which experiences the primary oscillations resulting from running, for example, as well as the secondary oscillations resulting from the inertia of the user's tissue, such as the breast. The measuring step 402 may therefore be seen broadly as covering not only one but more than one measurements performed with one or more sensors attached to various parts of the user.

Having established the oscillation parameters of the secondary oscillation data, an index value indicative of the support provided by the wearable garment 360 is calculated 407. The calculation may comprise detecting the most relevant peaks in the power spectrum and calculating their intensities. The ratio of the power of the main peak to the power of the secondary peaks can be monitored to detect the changes. Additionally or alternatively, the attenuation rate of the time domain signal after the main impact is an indication of the tightness of the garment. Also, the 'redshift' of the main frequencies in comparison to the initial/ideal status indicates the looseness of the garment.

Next, the index value may be compared 408 to a table or other data base comprising different support classes for each index value representing a course classification of the level of support. The support classes may include, for example, "sufficient", "moderate", "poor", "non-existent", etc. Based on the comparison 408, a support class is outputted 409 for the wearable garment 360. The outputting stage may include a signal transmitted by the sensor module 310, e.g. a light signal, a sound or haptic response provided that the sensor module is equipped with the necessary interface, or a message may be sent to the external device for display or another means of displaying the state of the wearable garment 360 to the user. Alternatively the output may simply prompt the external device to perform further analysis to the derived support class. Alternatively the calculated index value is outputted directly to the external device for display or further computing 410, 412, 411. In any case, it is preferable to save 412 the derived index value or support class or both into a built-in memory at the sensor module 310 or to a memory on an external device, cloud, server, etc.

Figure 5:
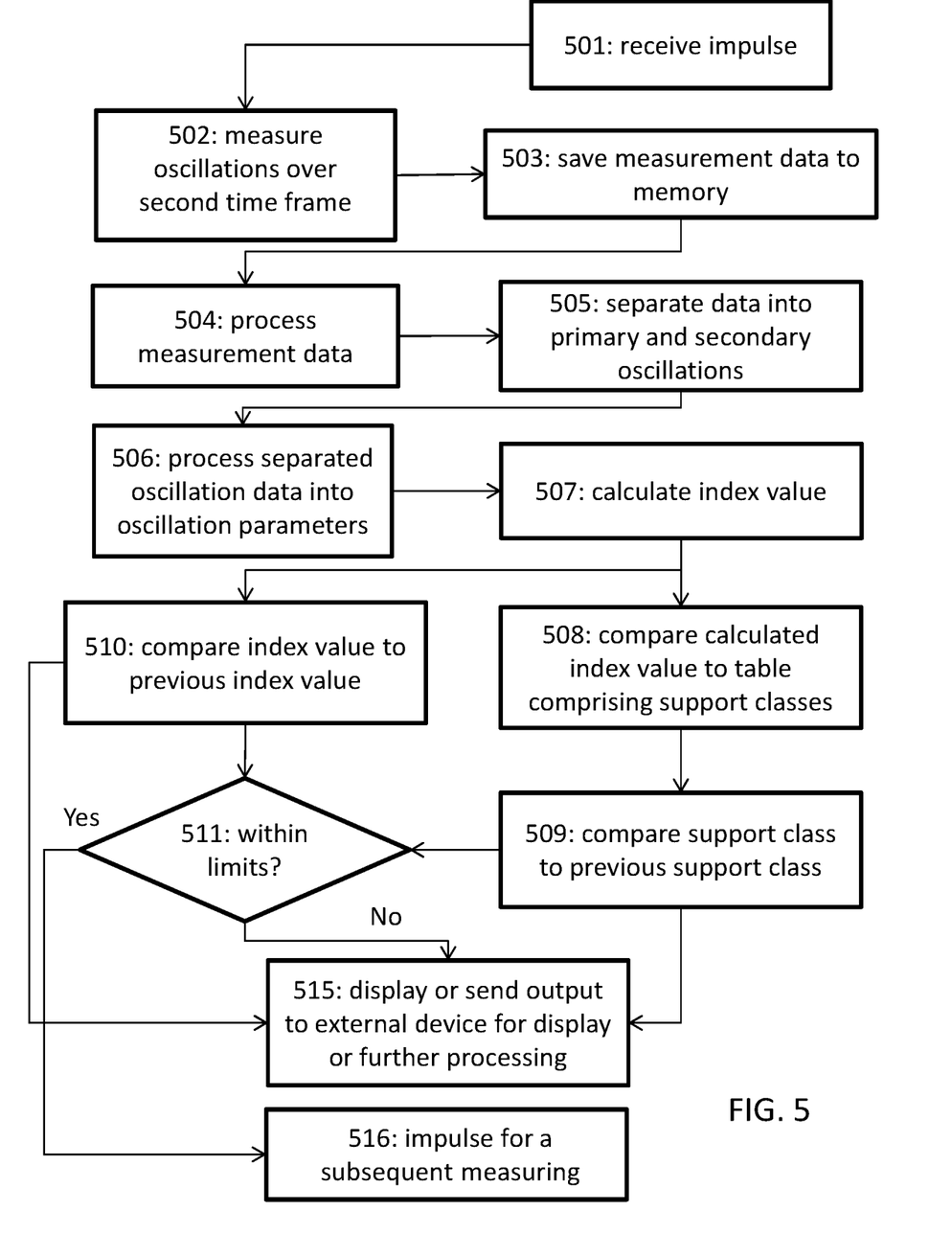
FIG. 5 is a flow graph showing further method steps according to one embodiment.

It is preferable to repeat the calculatory determination process in order to track the sufficiency of support of the wearable garment over time. FIG. 5 illustrates a broadly similar method for subsequent analysis cycles. The second and subsequent cycles may have similar impulses or excitations as the first cycle depicted in FIG. 4, but it may also be triggered automatically by any of the output steps 409, 410, 411, 412 of the previous cycle. The measuring step 502 is similar to the first measuring step 402 with the exception that it occurs at a different point in time and may have a different duration. For example, the first analysis cycle may be long to establish, whether or not this particular garment fits the user, whereas the subsequent analysis cycles may be periodic and brief so as to ascertain that the circumstances have not changed outside a tolerance. Another foreseeable option is to measure the oscillations during heart rate monitoring, wherein the user is likely to experience oscillation. According to a particular embodiment, the processor is configured to trigger oscillation measurement as a response to initiating heart rate measuring. The heart rate may be measured optically by, i.e. by using an optical heart rate (OHR) sensor, which may be attached integrally or detachably to the garment, elsewhere on the user or in a terminal device, such as a smart watch. In the event the heart rate sensor is external in respect to the sensor unit, the measurement data is transmitted preferably wirelessly to the processor hosted by the sensor unit, terminal device, cloud, or similar computing unit.

The saving 503, processing 504, analysing 505-509 steps are similar to the first cycle. However, the second and subsequent cycles may include an analysis step so as to determine, if the support has changed in respect to the previous analysis. Accordingly, the processor may compare 510 the results of the current computation to the previous or original or any preceding value. In addition or alternatively, the result, i.e. index value or support class may be compared to a predetermined limit stored into the memory. If the current result is within the predetermined limits 511, the process is repeated 516 and/or the result is displayed or further analysed 515. If the current result is outside the predetermined limits 511, the user is alerted by, for example, displaying a message on the screen of the terminal device. Furthermore, the processing unit may be programmed to transmit a message to a third party holding an account for the user to prompt an offer to replace the garment. Such an arrangement would be particularly useful as an interface to an online store. It is to be noted that the step 511 may also be performed in the first analysis cycle.

A simple example of analysing whether or not the supporting properties of the wearable garment have diminished would be to record the amplitude of the secondary oscillations over time and to alert the user, if the highest recorded amplitude is exceeded. This would be an indication of the tissue now being allowed to move more than before. The calculation could be programmed to allow several exceedings before concluding that the support is not sufficient.

As mentioned before, the wearable garment 360 may include an identification module 309 carrying information identifying the particular wearable garment 360. This information is preferably saved and associated with the present measurement and analysis data so as to track the condition and/or suitability of each garment in the user's wardrobe. The system may include a database containing usage information about each tracked item. The processor may then be programmed to prompt an alert to the user, if a particular garment has exceeded the pre-determined estimated life time for that product. With the permission of the user, this information may be conveyed to third parties, such as online stores.

According to a particular embodiment, the program or script to perform the necessary analysis computation may be stored in the internal memory of the sensor module 310, it may be stored to the memory of the external device performing the processing, or it may be downloaded. The processing instructions are preferably stored in and/or provided to the wireless communication unit as stand-alone applications, which can be run by the operating system (firmware) of the module. This allows for very generic modules still suitable for a variety of uses to be manufactured.

Figure 6:
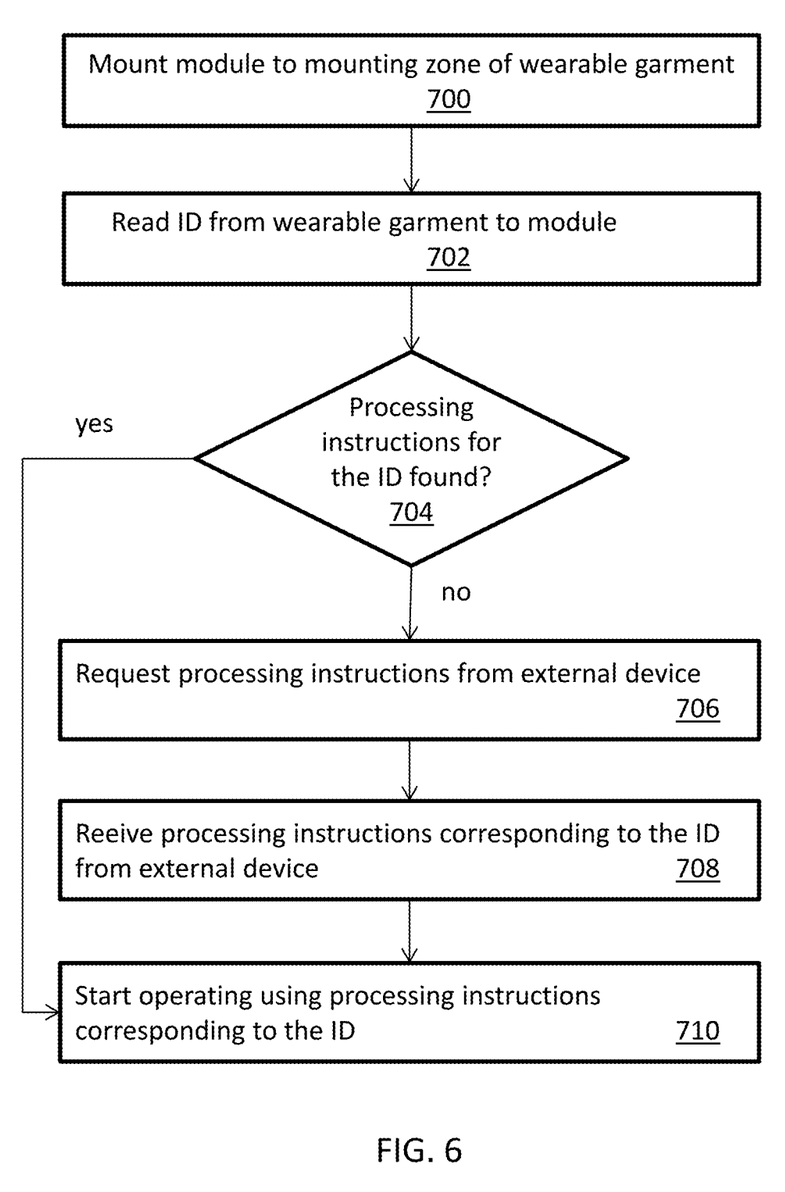
FIG. 6 shows a flow chart of the downloading embodiment.

FIG. 6 shows a flow chart of the downloading embodiment. First, in step 700, the sensor module 310 is mounted to a mounting zone of a wearable garment 360 designed to receive and hold the communication module thereon. The module makes electrical contact with the mounting zone via its contact terminals. Next, in step 702, the identification module 309 of the mounting zone is read by the sensor module 310, preferably via the electrical contact. Then, in step 704, the sensor module 310 checks if it is able to find processing instructions corresponding to the identification module 309 read in step 702 from its own memory. If correct instructions are found, they are taken into use and the module is adapted according to the instructions. Then, the operation can be started in step 710. If, on the other hand, the sensor module 310 does not readily contain the correct instructions, it sends the identifier to an external device, such as a wristop monitoring unit, smart phone, server, cloud, etc., together with a request for instructions in step 706. The device processes the request and responds by sending the correct instructions to the module in a suitable format. In step 708, the module receives the instructions, before adapting its operation accordingly and starting of operation in step 710.

According to a particular embodiment, the sensor module 310 or a terminal device comprised in the system may receive a new machine readable instruction for monitoring support from an external source via the wireless communication unit 314. It may be that a server, cloud or other external source contains an improved analysis script or program or similar for analyzing the oscillation data. The sensor module 310 or terminal device will then store the new machine readable instruction for monitoring support to the memory thereof and to run new machine readable instruction on the processor for monitoring the sufficiency of support provided by the wearable garment (360) according to the new machine readable instruction for monitoring support.

In the examples above, only wearable garments containing sensors functionally connectable with the communication module are discussed for simplicity. However, instead of or in addition to sensors, the sports items may contain actuators of any kind. An actuator differs from a sensor in that it produces a noticeable output for the user, whereas a sensor provides measurement information for the communication module to process and forward. The output may be visual, audible or mechanical (involving motion), for example.

In addition or as an alternative to downloading a particular program or script of analyzing the sufficiency of support based on oscillation measurement, the external device may also make adjustments to the measurement. For example, provided that heart beat or other physiological data is transmitted to the external device controlling the sensor device 310, the external device may adjust the sampling rate of the sensor device 310. Let us consider an example, where the external device receives heart beat data from the sensor module 310 (provided that it is equipped with a heartbeat sensor) or from a separate co-operating transmitter belt or wrist top device that the user has an elevated heart rate, the sensor module 310 may be controlled to increase the sample rate. This embodiment yields the effect that the sensor module 310 may be hibernate most of the time and only be prompted to take measurements, when the user is engaging in physical exercise thus saving energy. Instead of heart beat, the impulse may be a particular geographical location, such as a track, gym or similar location likely to induce exercise.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In this description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

| REFERENCE SIGNS LIST | |
|---|---|
| 200 | wireless link |
| 301A | EMG sensor pad |
| 301B | EMG sensor pad |
| 303 | mounting zone |
| 305A | wiring |
| 305B | wiring |
| 307A | counterpart |
| 307B | counterpart |
| 310 | sensor module |
| 311A | contact terminal |
| 311B | contact terminal |
| 312 | processor |
| 314 | wireless communication unit |
| 316 | power source |
| 317 | housing |
| 318 | oscillation sensing element |
| 360 | wearable garment |
| 401 | receive impulse |
| 402 | measure oscillation over first time frame |
| 403 | save measurement data to memory |
| 404 | process measurement data |
| 405 | separate data into primary and secondary oscillations |
| 406 | process data into oscillation parameters |
| 407 | calculate index value |
| 408 | compare calculated index value to table |
| 409 | output support class |
| 410 | output index value |
| 411 | display or send for processing |
| 412 | save to memory |
| 501 | receive impulse |
| 502 | measure oscillation over second time frame |
| 503 | save measurement data to memory |
| 504 | process measurement data |
| 505 | separate data into primary and secondary oscillations |
| 506 | process data into oscillation parameters |
| 507 | calculate index value |
| 508 | compare calculated index value to table |
| 509 | compare present support class to previous support class |
| 510 | compare present index value to previous index value |
| 511 | comparison if new value within predetermined limits |
| 515 | display or send for processing |
| 516 | impulse for a subsequent measuring |

CITATION LIST

Patent Literature

U.S. Pat. No. 6,198,204 B1

The invention claimed is:

1. A wearable garment comprising:
a sensor module attached to the wearable garment, the sensor module comprising an oscillation sensing element being configured to measure oscillations experienced by the wearable garment,
a processor, and
an interface provided to the oscillation sensing element for outputting measurement data to the processor, wherein
the processor is configured to process logged measurement data received via the interface by:
separating the measurement data into primary oscillations and secondary oscillations,
processing the measurement data of the primary and secondary oscillations into oscillation parameters, and
a calculating an index value representative of the parameters of the primary and secondary oscillation.

2. The wearable garment according to claim 1, wherein the oscillation sensing element comprises at least one of: an accelerometer, a multiple axis motion sensor, and a 9-axis motion sensor.

3. The wearable garment according to claim 1, wherein the sensor module comprises a wireless communication unit configured to directly or indirectly transmit and receive data to and from an external source.

4. The wearable garment according to claim 1, wherein the wearable garment further comprises:
an identification module comprising:
identification data stored thereon about the individual wearable garment, and
a communication interface configured to communicate the identification data,
and
a communication interface configured to read the identification data from the identification module.

5. The wearable garment according to claim 4, wherein the sensor module is configured to log the usage of the identified wearable garment in duration or oscillations or both.

6. The wearable garment according to claim 1, wherein the wearable garment is a brassiere.

7. The wearable garment according to claim 1, wherein the wearable garment further comprises a:
heart rate sensor, and
a sensor module configured to measure the sufficiency of support provided by a wearable garment.

8. The wearable garment according to claim 1, wherein the sensor module is integrated into the wearable garment.

9. The wearable garment according to claim 1, wherein the sensor module comprises a wireless communication unit configured to directly or indirectly transmit and receive data to and from a server or a terminal device or both from a server or a terminal device.

10. The wearable garment according to claim 1, wherein the wearable garment is a sports bra.

11. A system for determining the support provided by a wearable garment, the system comprising:
a processor,
a wearable garment comprising:
a sensor module attached to the wearable garment, the sensor module comprising an oscillation sensing element being configured to measure oscillations experienced by the wearable garment, and
an interface provided to the oscillation sensing element for outputting measurement data to the processor,
a memory for logging the measurement data, wherein
the processor is configured to process the logged measurement data received via the interface by:
separating the measurement data into primary oscillations and secondary oscillations
processing the measurement data of the primary and secondary oscillations into oscillation parameters, and
calculating an index value representative of the parameters of the primary and secondary oscillation.

12. The system according to claim 11, wherein:
the memory for logging the measurement data is a built-in memory of the sensor module or an external memory in respect to the sensor module, and wherein
the processor is a built-in processor of the sensor module or an external processor in respect to the sensor module.

13. The system according to claim 11, wherein:
the system comprises a processor external in respect to the sensor module, and wherein
the interface between the oscillation sensing element and the processor is a wireless link provided by the wireless communication unit.

14. The system according to claim 11, wherein the system further comprises a terminal device which in turn comprises the processor configured to perform at least some of the data processing steps or the memory or both.

15. The system according to claim 11, wherein the system is configured to:
receive a new machine readable instruction for monitoring support from an external source via the wireless communication unit,
store the new machine readable instruction for monitoring support to the memory, and
run the new machine readable instruction on the processor for monitoring the sufficiency of support provided by the wearable garment according to the new machine readable instruction for monitoring support.

16. The system according to claim 11, wherein the processor is configured to:
compile a message based at least partly on the oscillation data,
cause the message to be transmitted from the apparatus hosting the processor,
cause receiving in the apparatus of a machine readable instruction, and
derive an estimated activity type, using the machine readable instruction, based at least partly on the oscillation data.

17. The system according to claim 11, wherein the memory includes a computer program configured to control the apparatus to perform a method of computing the sufficiency of support provided by a wearable garment, which includes a sensor module being configured to measure oscillations experienced by the wearable garment, the method comprising the steps of:
measuring oscillations with the sensor module over a first time frame,
forming an output of the measurement data for a processor, and processing the measurement data with the processor into an index value representative of the support provided by the wearable garment.

18. The system according to claim 14, wherein the terminal device is a smart phone or wristop computer.

19. A method of computing the sufficiency of support provided by a wearable garment, which includes a sensor module being configured to measure oscillations experienced by the wearable garment, the method comprising the steps of:
measuring oscillations with the sensor module over a first time frame,
forming an output of the measurement data for a processor, and
processing the measurement data with the processor into an index value representative of the support provided by the wearable garment, wherein the processing comprises:
separating the measurement data into primary oscillations and secondary oscillations,
processing the measurement data of the primary and secondary oscillations into oscillation parameters, and
calculating an index value representative of the parameters of the primary and secondary oscillation.

20. The method according to claim 19, wherein the oscillation parameters are selected from a list comprising:
frequency,
amplitude, and
phase shift.

21. The method according to claim 19, further comprising outputting the calculated index value as an indication of support provided by the wearable garment.

22. The method according to claim 19, wherein the processing comprises:
comparing the index value to a table comprising support classes for various index value ranges, and
outputting a computed support class based on the comparison.

23. The method according to claim 19, wherein the method further comprises:
saving a calculated index value or support class gathered over the first time frame into a memory as a reference value,
repeating the processing of measurement data over a second time frame, and
comparing the index value or support class of the second time to the corresponding saved reference value of the first time frame, and:
when the change in index value is inside pre-determined limits, continuing to repeat the processing of measurement data over a third time frame, or
when the change in index value is outside pre-determined limits, outputting a signal representative of a change in support.

24. The method according to claim 19, wherein the measuring is triggered by an impulse detected by the sensor module or by an external sensor.

25. The method according to claim 19, wherein:
a new machine readable instruction for monitoring support is received from an external source via the wireless communication unit,
the new machine readable instruction for monitoring support is stored to the memory, and
the new machine readable instruction is run on the processor for monitoring the sufficiency of support provided by the wearable garment according to the new machine readable instruction for monitoring support.

26. The method according claim 19, wherein the method further comprises:
reading identification data stored on an identification module of the wearable garment,
logging the usage of the identified wearable garment in duration or oscillations or both, and
processing the logged usage data into an index value representative of the support provided by the wearable garment.

27. A non-transitory computer readable medium having stored thereon a set of computer readable instructions that, when executed by at least one processor, cause an apparatus to at least:
receive oscillation measurement data, and
process the measurement data with the processor into an index value representative of the support provided by a wearable garment by:
separating the measurement data into primary oscillations and secondary oscillations,
processing the measurement data of the primary and secondary oscillations into oscillation parameters, and
calculating an index value representative of the parameters of the primary and secondary oscillation.

28. The non-transitory computer readable medium according to claim 27, wherein the instructions are configured, when executed by at least one processor, cause an apparatus to perform a method of computing the sufficiency of support provided by a wearable garment, which includes a sensor module being configured to measure oscillations experienced by the wearable garment, the method comprising the steps of:
measuring oscillations with the sensor module over a first time frame,
forming an output of the measurement data for a processor, and
processing the measurement data with the processor into an index value representative of the support provided by the wearable garment.

29. The method according to claim 19, wherein the impulse is an elevated pulse or oscillation exceeding a predetermined limit.

* * * * *